United States Patent [19]

Onsager

[11] 3,956,358
[45] May 11, 1976

[54] DIMERIZATION METHOD

[75] Inventor: Olav Torgeir Onsager, Suffern, N.Y.

[73] Assignee: Halcon International, Inc., New York, N.Y.

[22] Filed: Dec. 30, 1974

[21] Appl. No.: 537,297

[52] U.S. Cl. .................. 260/465.8 D; 260/485 R
[51] Int. Cl.² ............... C07C 120/00; C07C 69/52
[58] Field of Search ............... 260/465.8 D, 485 R

[56] References Cited
UNITED STATES PATENTS

| | | | |
|---|---|---|---|
| 3,484,475 | 12/1969 | Cornforth et al. | 260/465.8 D |
| 3,499,024 | 3/1970 | Morita et al. | 260/465.8 D |
| 3,567,760 | 3/1971 | Feldman et al. | 260/465.8 D |
| 3,733,351 | 5/1973 | Watanabe et al. | 260/465.8 D |

*Primary Examiner*—Joseph P. Brust
*Attorney, Agent, or Firm*—William C. Long; Riggs T. Stewart; David Dick

[57] ABSTRACT

Derivatives of the α,β-unsaturated carboxylic acids are dimerized by reaction in the presence of a catalyst consisting essentially of (a) at least one metal compound of the formula $M(X)_n$ wherein M is zinc, aluminum, titanium, vanadium, iron, or cobalt, X is a halide and n is a number equal to the valence of the metal M and (b) at least one nitrogen-containing Lewis Base which is (1) a tertiary monoaryl amine of the formula,

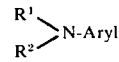

wherein $R^1$ and $R^2$ are the same or different and each is an alkyl group or a cycloalkyl group with at least one of $R^1$ and $R^2$ containing at least two carbon atoms; or (2) a tertiary monobenzyl amine of the formula,

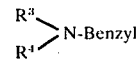

wherein $R^3$ and $R^4$ are the same or different and each is an alkyl or cycloalkyl radical; or (3) a tertiary di- or poly-functional amine which contains at least two Lewis Base nitrogen groups which are separated from each other by at least one carbon atom, and are (a) N-disubstituted amino groups wherein each N-substituent is the same or different and is an alkyl, cycloalkyl, benzyl, aryl radical or (b) N-heterocyclic groups containing 3 to 20 carbon atoms; or (4) an N-substituted heterocyclic amine wherein the N-substituent is an alkyl, benzyl, cycloalkyl or aryl radical.

6 Claims, No Drawings

DIMERIZATION METHOD

This invention relates to the dimerization of α,β-unsaturated carboxylic acid derivatives and is more particularly concerned with the dimerization of the nitrile and esters of acrylic acid.

The dimerization of certain α,β-unsaturated carboxylic acid derivatives is a known reaction. For example, acrylonitrile can be dimerized in the presence of a catalyst to produce 2-methylene glutaronitrile (2-MGN). Such dimerization is commonly referred to as "head-to-tail" dimerization since in the dimer the α-carbon atom of one monomer molecule is attached to the β-carbon atom of the other monomer molecule. Various tertiary phosphines, certain types of cyclic tertiary amines having at least one nitrogen atom common to two or three rings e.g. triethylenediamine (British Pat. No. 1,168,774) and a wide variety of metal carbonyls are known to be suitable for use as catalysts in this reaction. Furthermore, the use of a catalyst system composed of at least one metal halide of the formula $MX_n$ in which M is zinc, aluminum, titanium, vanadium, iron or cobalt, X is a halogen, and $n$ is a number equal to the valence of the metal M. and at least one trialkylamine of the formula

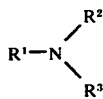

in which $R^1$, $R^2$, and $R^3$ are alkyl groups, is known (British Pat. No. 1,256,392 and U.S. Pat. No. 3,733,351).

The object of the present invention is to provide an improved process for the head-to-tail dimerization of α,β-unsaturated carboxylic acid derivatives characterized by the use of a novel catalyst system.

It is a further object of the invention to provide a process of the character indicated which is particularly applicable to the head-to-tail dimerization of acrylonitrile to produce 2-methylene glutaronitrile.

In accordance with the invention, α,β-unsaturated carboxylic acid derivatives are dimerized in the presence of a catalyst which consists essentially of (a) at least one metal compound of the formula $M(X)_n$ wherein M is zinc, aluminum, titanium, vanadium, iron or cobalt, X is a halide, and n is a number equal to the valence of the metal M and (b) at least one nitrogen-containing Lewis Base which is (1) a tertiary monoaryl amine of the formula

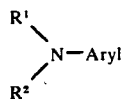

wherein $R^1$ and $R^2$ are the same or different and each is an alkyl group or a cycloalkyl group with at least one of the R radicals containing at least two carbon atoms; or (2) a tertiarymonobenzyl amine of the formula,

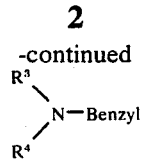

wherein $R^3$ and $R^4$ are the same or different each is an alkyl or cycloalkyl radical; or (3) a tertiary di- or polyfunctional amine which contains at least two Lewis Base nitrogen groups which are separated from each other by at least one carbon atom and are (a) N-disubstituted amino groups wherein each N-substituent is the same or different and is an alkyl, cycloalkyl, benzyl, aryl radical or (b) N-heterocyclic groups containing 3 to 20 carbon atoms; or (4) an N-substituted heterocyclic amine wherein the N-substituent is an alkyl, benzyl, cycloalkyl or aryl radical.

Preferably, the alkyl radicals have 1 to 20 carbon atoms, the cycloalkyl radicals have 4 to 12 carbon atoms, the benzyl radicals have 7 to 20 carbon atoms, the aryl radicals have 6 to 20 carbon atoms and the heterocyclid radicals have 3 to 20 carbon atoms. The aryl radical of the monoaryl amines and the benzyl radical of the monobenzyl amines may be unsubstituted or substituted. Preferred substituents are alkyl and cycloalkyl radicals or combinations thereof, containing up to 20 carbon atoms. In addition, all the radicals, including the heterocyclic rings, may contain non-reactive groups, e.g. nitrile, ether and ester-groups.

The halogen of the (a) component of the catalyst is preferably chlorine, bromine or iodine and typical examples of the (a) component having the formula $M(X)_n$ include $ZnCl_2$, $ZnBr_2$, $ZnI_2$, $AlCl_3$, 3, $TiCl_3$, $TiCl_4$, $TiBr_4$, $VCl_3$, $FeI_2$, $CoBr_2$, and $CoI_2$. The preferred metals are zinc and aluminum.

Typical Lewis Bases suitable for use as the (b) component of the catalyst system of the invention include tertiary monoaryl amines such as N,N-diethyl-aniline, N-ethyl-N-methylparatolylamine, N,N-dipropylaniline, and N,N-diethylmesitylamine; tertiary monobenzyl amines such as N,N-dimethylbenzylamine, N,N-diethylbenzylamine, and N,N-dicyclohexylbenzylamine, tertiary di- and poly-amines such as $N,N,N^1$, $N^1$ tetraethyl-1, 6-hexanediamine, methylenedipiperidine, N,N-diethylaminomethyl-polystyrene and p-(N,N-diethylamino)-N, N-diethylaniline, tertiary heterocyclic amines such as N-methylpiperidine, N-ethylpiperidine, N-cyclohexylpiperidine, N-phenylpiperidine, N-benzylpiperidine, N-ethylmorpholine, $N,N^1$-dimethylpiperazine, and N-methylpyrrolidine. The most preferred Lewis Bases are those which are tertiary monoaryl amines, tertiary monobenzyl amines and heterocyclic amines.

It should be understood that the specific (a) and (b) catalyst components identified above are merely representative of suitable compounds and the invention is not limited to these specific compounds but includes like compounds within the generic definition of the (a) and (b) compounds.

The monomers suitable for use in the process of the invention include acrylonitrile and the lower alkyl (1-4 carbon atoms) and phenyl esters of acrylic acid. Examples of such esters include methylacrylate, ethylacrylate, n-propyl acrylate, n-butyl acrylate and phenyl acrylate. The preferred monomer is acrylonitrile by itself and, as previously mentioned, the process of the invention is particularly applicable to the head-to-tail dimerization of acrylonitrile to produce 2-MGN.

That the above-defined tertiary aromatic amines, the teritary benzyl amines and the heterocyclic amines have been found to be highly active catalyst components for dimerization is particularly surprising in view of the data reported in U.S. Pat. No. 3,733,351 in which it is stated that related compounds are inactive (Ref. Table 5, Ex. 3 and 5) or yield high polymers (Ref. Table 5, Ex. 7) rather than the desired dimer product.

The molar ratio between the Lewis base component and the metal salt component can vary widely. In general, the Lewis base/metal salt mole ratio is from 0.1 to 25, preferably 0.5 to 20, per mole of metal salt.

The concentration of the metal salt in the reaction zone is suitably selected to give a practical rate of reaction. It has been found that the rate of reaction increases with increasing metal salt concentrations. In general, the metal salt concentration is advantageously from 0.5 to 20 wt. %, the preferred concentration being from 1.0 to 15 wt. %, based on the weight of the liquid-phase reaction mixture.

The catalyst system may be soluble or (at least in part) insoluble in the reaction mixture. A solvent can be used, if desired, but is not necessary for carrying out the dimerization reaction. Preferred solvents are aliphatic or aromatic nitriles, hydrocarbons, especially aromatic hydrocarbons, chlorohydrocarbons, ethers, sulfoxides and like organic solvents inert in the dimerization reaction. Examples of preferred solvents include acetonitrile, propionitrile, hexane, hexadecane, benzonitrile, benzene, p-xylene, o-dichlorobenzene, sulfolane and dimethylsulfoxide. The amount of solvent, when used, is suitably 5–80 wt. % of the liquid reaction mixture.

The two catalyst compounds can be added separately to the reaction zone or they can be premixed before addition. Furthermore, if desired, one or both components can be dissolved in an inert solvent and fed to the reaction zone in the form of a solution.

The pressure and temperature are selected so as to maintain the monomer being dimerized in the liquid phase during the reaction. In general, the temperature is within the range of from 10° to 150°C, the most preferred temperature being from 20° to 100°C. The pressure will, of course, vary with the temperature and typically will be within the range of 0.1 atm. to 100 atm. preferably 1 atm. to 10 atm.

If desired, a polymerization inhibitor for the monomer can be used. Such inhibitors are well known and typical inhibitors include hydroquinone, methylene blue, and p-nitrosodimethylaniline. Very small amounts of inhibitor can be employed, e.g. 5 to 1000 ppm based on the weight of the monomer.

The process according to the invention can be carried out as a batch process or in continuous fashion. The residence time is selected to give at least 1 wt. % dimer product in the liquid-phase reaction mixture. The concentration of dimer is readily determined by conventional analytical procedures such as gas/liquid chromatography. In general, residence times of less than 10 hours are employed, the preferred residence time being less than 6 hours. In general, a residence time of at least 5 minutes is normally employed.

The dimer product is recovered from the reaction product by conventional means such as distillation or solvent extraction. The catalyst can be reused, if desired, by recycling either or both of the two components, after the dimer and unreacted monomer have been separated from them.

In order to obtain improved rates of reaction the reaction system should be kept substantially anhydrous.

The process of the invention will be more fully understood by reference to the following examples which are given for illustrative purposes only and are not to be interpreted as limitative of the invention.

EXAMPLE 1

Two grams of $AlCl_3$ (anhydrous) 25 ml of acrylonitrile (containing 100 ppm hydroquinone) and 4 ml of N-methylpiperidine are charged to a 100 ml glass reactor equipped with thermometer, condenser and magnetic stirrer. The reactor is placed in a constant temperature water bath and the mixture allowed to react for 16 hours at 30°C. The effluent is then analyzed by gas/liquid chromatography for 2-methyleneglutaronitrile. The yield of 2-methyleneglutaronitrile is 62.5% based on the total amount of acrylonitrile charged to the reactor. The effluent is flash distilled at reduced pressure. The in hand yield of 2-methyleneglutaronitrile is 52.0% collected as the cut distilling between 130°C and 135°C at 10 mmHg pressure.

In the following examples, as in this example, the dimer is essentially the only product formed and trimer and polymer, if detectable at all, are present in very small amounts, demonstrating the highly selective nature of the catalyst in producing dimer.

EXAMPLES 2–12

Using the same general procedure described in Example 1, a series of experiments are carried out. The feed composition, the conditions of reaction and the data obtained are summarized in Table 1. The 2-methyleneglutaronitrile (2MGN) yields reported in this table are determined by gas/liquid chromatographic analysis and are based on the total amount of acrylonitrile charged to the reactor.

EXAMPLE 13

Two grams of $AlCl_3$ (anhydrous), 12.5 ml methylacrylate 12.5 ml acetonitrile (solvent) and 4.0 ml of N-methylpiperidine are charged to a 100 ml glass reaction flask equipped with thermometer, condenser and magnetic agitation. The reaction flask is placed in a constant-temperature water bath and the mixture allowed to react for 16 hours at 50°C. The effluent is then cooled to room temperature and analyzed by gas/liquid chromatography for 2-methyleneglutaric acid dimethyl ester. The 2-methyleneglutaric acid dimethyl ester yield was 5.0% based on the total amount of methylacrylate charged to the reaction flask.

TABLE 1

| EXAMPLE NO. | FEED COMPOSITION | | | | CONDITIONS | | 2 MGN YIELD % |
|---|---|---|---|---|---|---|---|
| | ACRYLONITRILE ML. | LEWIS BASE GRS. | SALT GRS. | SOLVENT ML. | TIME HRS. | TEMP. °C | |
| 2 | 25 | N,N diethylaniline 3.0 | $ZnCl_2$ 2.0 | None | 16 | 30 | 26.2 |

TABLE 1-continued

| EXAMPLE NO. | FEED COMPOSITION | | | CONDITIONS | | | 2 MGN YIELD % |
|---|---|---|---|---|---|---|---|
| | ACRYLONITRILE ML. | LEWIS BASE GRS. | SALT GRS. | SOLVENT ML. | TIME HRS. | TEMP. °C | |
| 3 | 25 | N,N dimethylbenzylamine 4.0 | $ZnCl_2$ 2.0 | None | 16 | 30 | 37.0 |
| 4 | 25 | Diethylaminomethyl-polystyrene * 4.0 | $ZnCl_2$ 4.0 | None | 16 | 50 | 15.0 |
| 5 | 25 | N-methylpiperidine 3.0 | VCl 2.0 | None | 16 | 25 | 6.2 |
| 6 | 25 | N,N' dimethylpiperazine 3.0 | $TiCl_3$ 4.0 | None | 16 | 50 | 1 |
| 7 | 25 | N,N' dimethylpiperazine 3.0 | $TiCl_2$ 4.0 | None | 16 | 50 | 2 |
| 8 | 25 | N,N' dimethylpiperazine 3.0 | $CoBr_2$ 4.0 | None | 16 | 50 | 1 |
| 9 | 25 | N,N-dimethyl-p-tolylamine 4.0 | $ZnI_2$ 4.0 | Sulfolane | 3 | 60 | 34.0 |
| 10 | 25 | N-phenylpiperidine 4.0 | $AlCl_3$ 4.0 | None | 22 | 50 | 22.1 |
| 11 | 25 | N-methylpiperidine 6.0 | $AlBr_3$ 2.0 | Acetonitrile | 16 | 30 | 48.0 |
| 12 | 25 | N-methylmorpholine 3.0 | $ZnCl_2$ 2.0 | None | 16 | 25 | 11.2 |

* Diethylaminomethyl polystyrene: 3 meqv. base/gr. of resin

In the foregoing examples the term "yield" has its usual meaning and can be expressed as follows:

$$\% \text{ yield} = \frac{\text{weight dimer produced}}{\text{weight monomer charged}} \times 100$$

It will be apparent that various changes and modifications may be made without departing from the invention as defined in the appended claims and it is intended, therefore, that all matter contained in the foregoing description shall be interpreted as illustrative only and not as limitative of the invention.

What is claimed is:

1. A process for the dimerization of an α,β-unsaturated carboxylic acid derivative which is acrylonitrile or a lower alkyl or phenyl ester of acrylic acid to produce 2-methylene glutaronitrile or a lower alkyl or phenyl ester of 2-methylene glutaric acid which comprises reacting said derivative in the liquid phase at a temperature of 10° to 150°C. in the presence of a catalyst consisting essentially of (a) at least one metal compound of the formula $M(X)_n$ wherein M is zinc, aluminum, titanium, vanadium, iron, or cobalt, X is a halide and n is a number equal to the valence of the metal M; and (b) at least one nitrogen-containing Lewis Base which is (1) a tertiary monoaryl amine of the formula

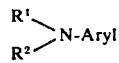

wherein $R^1$ and $R^2$ are the same or different and each is an alkyl group or a cycloalkyl group with at least one of $R^1$ and $R^2$ containing at least two carbon atoms; or (2) a tertiary monobenzyl amine of the formula

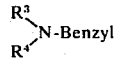

wherein $R^3$ and $R^4$ are the same or different and each is an alkyl or cycloalkyl radical; or (3) a tertiary polyfunctional amine wich contains at least two Lewis Base nitrogen groups which are separated from each other by at least one carbon atom, and are (a) N-substituted amino groups wherein each N-substituent is the same or different and is an alkyl, cycloalkyl, benzyl, aryl radical or (b) N-heterocyclyc groups containing 3 to 20 carbon atoms; or (4) a mono nitrogen-containing N-substituted heterocyclic amine wherein the N-substituent is an alkyl, benzyl, cycloalkyl or aryl radical, wherein the Lewis Base/metal compound mole ratio is from 0.1:1 to 25:1, each radical and each heterocyclic group or ring may be unsubstituted or substituted by non-reactive groups, each alkyl radical contains 1 to 20 carbon atoms and each aryl radical contains 6 to 20 carbon atoms.

2. A process as defined in claim 1, wherein the metal M is zinc or aluminum.

3. A process as defined in claim 1, wherein the Lewis Base is a tertiary monoaryl amine, a tertiary monobenzyl amine, or a heterocyclic amine.

4. A process as defined in claim 1, wherein the α,β-unsaturated carboxylic acid derivative is a lower alkyl ester of acrylic acid.

5. A process as defined in claim 1, wherein the α,β-unsaturated carboxylic acid derivative is acrylonitrile.

6. A process as defined in claim 1, wherein the α,β-unsaturated carboxylic acid derivative is acrylonitrile, the metal M is zinc or aluminum, and the Lewis Base is a tertiary monoaryl amine, a tertiary monobenzyl amine or a heterocyclic amine.

* * * * *